(12) United States Patent
Ghassemzadeh et al.

(10) Patent No.: US 9,418,342 B2
(45) Date of Patent: Aug. 16, 2016

(54) METHOD AND APPARATUS FOR DETECTING MODE OF MOTION WITH PRINCIPAL COMPONENT ANALYSIS AND HIDDEN MARKOV MODEL

(71) Applicants: AT&T Intellectual Property I, L.P., Atlanta, GA (US); President and Fellows of Harvard College, Cambridge, MA (US)

(72) Inventors: Saeed S. Ghassemzadeh, Andover, NJ (US); Lusheng Ji, Randolph, NJ (US); Robert Raymond Miller, II, Convent Station, NJ (US); Manish Gupta, Cambridge, MA (US); Vahid Tarokh, Cambridge, MA (US)

(73) Assignees: AT&T Intellectual Property I, L.P., Atlanta, GA (US); President and Fellows of Harvard College, Cambridge, MA (US)

( * ) Notice: Subject to any disclaimer, the term of this patent is extended or adjusted under 35 U.S.C. 154(b) by 231 days.

(21) Appl. No.: 14/099,499

(22) Filed: Dec. 6, 2013

(65) Prior Publication Data

US 2015/0161516 A1     Jun. 11, 2015

(51) Int. Cl.
| | |
|---|---|
| *G06N 7/00* | (2006.01) |
| *G06N 5/04* | (2006.01) |
| *G06N 99/00* | (2010.01) |
| *G06F 19/00* | (2011.01) |

(52) U.S. Cl.
CPC .............. *G06N 99/005* (2013.01); *G06F 19/30* (2013.01); *G06N 5/04* (2013.01); *G06N 7/005* (2013.01)

(58) Field of Classification Search
None
See application file for complete search history.

(56) References Cited

U.S. PATENT DOCUMENTS

| 8,473,438 | B2 | 6/2013 | Potkonjak | |
|---|---|---|---|---|
| 2002/0128827 | A1* | 9/2002 | Bu | .......................... G10L 15/02 704/222 |
| 2006/0280235 | A1* | 12/2006 | Rhee | ..................... H04L 41/142 375/222 |
| 2006/0284979 | A1 | 12/2006 | Clarkson | |
| 2007/0263907 | A1* | 11/2007 | McMakin | ............. G01S 13/887 382/115 |
| 2008/0146968 | A1 | 6/2008 | Hanawaka et al. | |
| 2009/0137933 | A1 | 5/2009 | Lieberman et al. | |

(Continued)

OTHER PUBLICATIONS

Chen, M. et al. (2007). "Human abnormal gait modeling via hidden Markov model." Information Acquisition, 2007. ICIA'07. International Conference on. IEEE.DOI: 10.1109/ICIA.2007.4295787.*

(Continued)

*Primary Examiner* — Stanley K Hill
*Assistant Examiner* — Benjamin Buss (57) ABSTRACT

A method, computer-readable storage device and apparatus for determining a mode of motion are disclosed. For example, a method receives training data comprising gait information associated with a plurality of different modes of motion. The method performs principal component analysis on the training data to extract principal components from the training data and generates a hidden markov model for each of a plurality of different modes of motion based upon the training data. The method receives testing data comprising gait information, transforms the testing data based upon the principal components and calculates a likelihood of the testing data based upon each hidden markov model for each of the plurality of different modes of motion. The method determines the mode of motion of the testing data, where the mode of motion is one of the plurality of different modes of motion for which a highest likelihood is calculated.

20 Claims, 5 Drawing Sheets

(56) References Cited

U.S. PATENT DOCUMENTS

| | | | |
|---|---|---|---|
| 2010/0035688 A1 | 2/2010 | Picunko | |
| 2010/0035727 A1* | 2/2010 | Brunner | A61B 5/1038 482/8 |
| 2010/0070316 A1 | 3/2010 | Lieberman et al. | |
| 2011/0022349 A1 | 1/2011 | Stirling et al. | |
| 2011/0054359 A1 | 3/2011 | Sazonov et al. | |
| 2011/0161067 A1* | 6/2011 | Lesher | G06F 17/241 704/1 |
| 2011/0313714 A1 | 12/2011 | Lieberman et al. | |
| 2012/0035509 A1 | 2/2012 | Wilson et al. | |
| 2012/0254100 A1* | 10/2012 | Grokop | A61B 5/1123 706/52 |
| 2012/0254333 A1* | 10/2012 | Chandramouli | G06F 17/27 709/206 |
| 2012/0255160 A1 | 10/2012 | Boone et al. | |
| 2013/0103170 A1 | 4/2013 | Prstojevich | |
| 2013/0190903 A1 | 7/2013 | Balakrishnan et al. | |
| 2014/0195023 A1* | 7/2014 | Statham | A63B 69/0028 700/91 |
| 2015/0057808 A1* | 2/2015 | Cook | G06N 99/005 700/275 |

OTHER PUBLICATIONS

Wang, L. et al. (2003). "Silhouette analysis-based gait recognition for human identification." Pattern Analysis and Machine Intelligence, IEEE Transactions on 25.12: 1505-1518. DOI: 10.1109/TPAMI. 2003.1251144.*

Li, Y. et al (2012). "Semi-supervised Gait Recognition Based on Self-Training." Advanced Video and Signal-Based Surveillance (AVSS), 2012 IEEE Ninth International Conference on. IEEE. DOI: 10.1109/AVSS.2012.66.*

Bernecker, T. et al. (2012). "Activity Recognition on 3D Accelerometer Data (Technical Report)". 22 Pages.*

Suk, H-I. et al. (2006). "HMM-based gait recognition with human profiles." Structural, Syntactic, and Statistical Pattern Recognition. Springer Berlin Heidelberg. 596-603.*

Iwamoto, K. et al. (2003). "A Gait Recognition Method using HMM". SICE Annual Conference in Fukui. pp. 1936-1941.*

Wang, L. (2006). "Abnormal walking gait analysis using silhouette-masked flow histograms." Pattern Recognition, 2006. ICPR 2006. 18th International Conference on. vol. 3. IEEE. DOI: 10.1109/ICPR. 2006.199.*

Bae, J., et al., "Gait Phase Analysis Based on a Hidden Markov Model," *Mechatronics* 21.6, 2011, pp. 961-970.

Hollmen, J., "Mixture Modeling of Gait Patterns from Sensor Data," *Proceedings of the 5th International Conference on Pervasive Technologies Related to Assistive Environments*, ACM, 2012.

Bamberg, S., et al., "Gait Analysis Using a Shoe-Integrated Wireless sensor System," IEEE Transactions on *Information Technology in Biomedicine* 12.4, 2008, pp. 413-423.

* cited by examiner

METHOD AND APPARATUS FOR DETECTING MODE OF MOTION WITH PRINCIPAL COMPONENT ANALYSIS AND HIDDEN MARKOV MODEL

BACKGROUND

Pedometers are popular for use as everyday exercise accessories. Often worn on the belt, pedometers can record the number of steps that a user has walked, and thus the distance. Pedometers, or step counters, can provide encouragement to a user to compete with oneself in getting fit and losing weight. However, most pedometers do not have the ability to record and store data. In addition, such pedometers often erroneously record movements other than walking, such as bending to tie shoes, or a road bump while travelling in a vehicle. At the same time, falls are serious hazards for older individuals as coordination, muscle strength, and balance tend to deteriorate with age and advance of chronic diseases such as Parkinson's disease and the like. In managed care as well as home settings, injuries resulting from falls may render older individuals incapable of calling for help and/or requiring emergency treatment. Resulting bone fractures can require lengthy and costly treatment, severely impact quality of life, and can trigger a cascade of other factors that lead to a rapid decline of the health of an individual.

SUMMARY

In one embodiment, the present disclosure provides a method, computer-readable storage device, and apparatus for determining a mode of motion. For example, a method receives training data comprising gait information associated with a plurality of different modes of motion. The method then performs principal component analysis on the training data to extract principal components from the training data and generates a hidden markov model for each of a plurality of different modes of motion based upon the training data. The method further receives testing data comprising gait information, transforms the testing data based upon the principal components and calculates a likelihood of the testing data based upon each hidden markov model for each of the plurality of different modes of motion. The method then determines the mode of motion of the testing data, where the mode of motion is one of the plurality of different modes of motion for which a highest likelihood is calculated.

BRIEF DESCRIPTION OF THE DRAWINGS

The present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

The present disclosure relates generally to the tracking of physical activities and, more particularly, to a method, computer-readable storage device, and apparatus for determining a mode of motion using a Principal Component Analysis of gait information combined with the use of a Hidden Markov Model (HMM) for each of a plurality of different modes of motion. For example, in one embodiment different characteristics of human motion are detected through an analysis of a user's gait. The user's gait information is gathered from multiple sensors in the soles of the shoes of the user, collected and sent to a network-based monitoring server to perform gait analysis. In one embodiment, during a training phase, training data is generated from test subjects, e.g., multiple users performing known motions, stances and/or postures, e.g., running, jumping, standing, sitting, walking, falling, cycling, lying down, etc. A subset of the training data is used to determine "principal components" associated with different stages of each of the modes of motion for use in reducing the feature space. Each mode of motion is then modeled as a Hidden Markov Model (HMM). In particular, a subset of the training data is also used to determine emission probabilities and transition probabilities between different stages/phases in a gait cycle for each mode of motion (i.e., between the hidden states). Thus, each HMM may comprise a signature which uniquely identifies one of the different modes of motion. After the training phase, observed gait information of a user may then be subject to statistical analysis to determine a best matching signature/HMM. In other words, the current mode of motion is the one having the HMM that best predicts the currently observed gait information. A more detailed discussion of exemplary algorithms for determining a mode of motion, or activity type, follows below.

Figure 1:
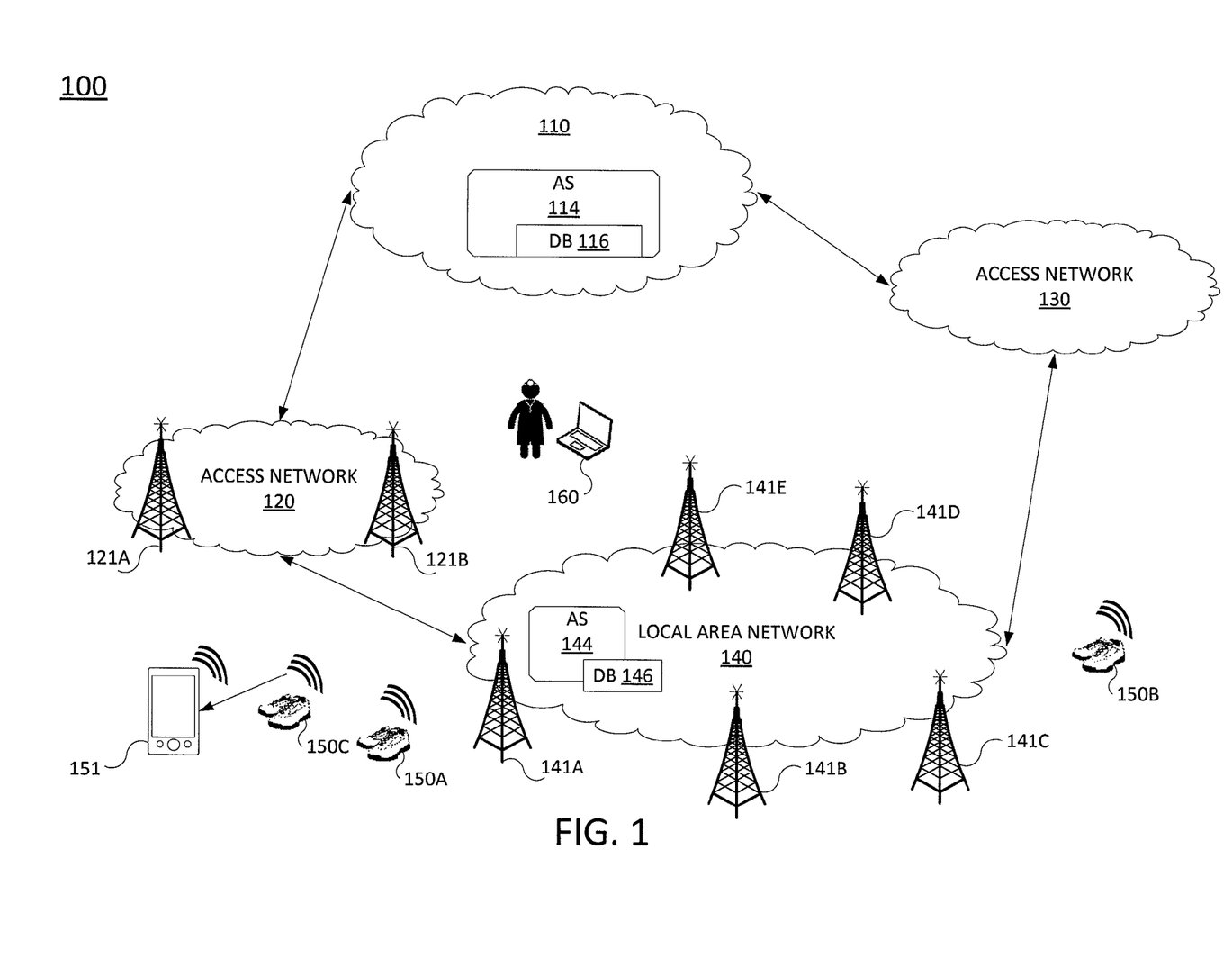
FIG. 1 illustrates one example of a communication network of the present disclosure.

To aid in understanding the present disclosure, FIG. 1 illustrates a block diagram depicting one example of a communication network 100 suitable for use in performing or enabling some or all of the features described herein. The communication network 100 may be any type of communication network, such as for example, a traditional circuit switched network (e.g., a public switched telephone network (PSTN)) or a packet network such as an Internet Protocol (IP) network (e.g., an IP Multimedia Subsystem (IMS) network), an asynchronous transfer mode (ATM) network, a wireless network, a cellular network (e.g., 2G, 3G, and the like), a long term evolution (LTE) network, and the like related to the current disclosure. It should be noted that an IP network is broadly defined as a network that uses Internet Protocol to exchange data packets.

In one embodiment, the network 100 may comprise a core network 110. The core network 110 may be in communication with one or more access networks 120 and 130. For instance, access network 120 may comprise a wireless access network (e.g., an IEEE 802.11/Wi-Fi network, a wide area network (WAN) and the like) or a cellular access network. Thus, in one example, access network 120 may include one or more wireless transceivers 121A and 121B, which may alternatively comprise cellular base stations, base transceiver stations (BTSs), NodeBs, evolved NodeBs (eNodeBs), wireless access points, and so forth. Similarly, access network 130 may comprise a wired access network such as a circuit switched access network, a cable access network, a digital subscriber line (DSL) access network, and so forth. The core network 110 and the access networks 120 and 130 may be operated by different service providers, the same service provider or a combination thereof.

In one embodiment, network 100 also includes a local area network (LAN) 140. For example, local area network 140 may comprise a wireless local area network (LAN), a Bluetooth network, a ZigBee network, and so forth. For instance, local area network 140 may be a home network or an office network, e.g., a network that is maintained by a hospital, an elder care facility, a rehabilitation center, and so forth. As illustrated, local area network 140 may comprise a coverage network or mesh network of ZigBee access points 141A-141E which may be connected to one another and to other devices and networks via an Ethernet network. However, it should be noted that ZigBee is designed for static end nodes. Thus, local area network 140 may comprise a ZigBee mesh network modified to enable handoffs between the different ZigBee access points 141A-141E.

In one example, the ZigBee access points 141A-141E are in communication with one or more sets of wearable devices 150A-150C. Each of the sets of wearable devices 150A-150C may comprise a pair of "smart" shoes, or shoe inserts. The term "smart" implies ability to measure, record, process, and communicate information. In addition, each of the sets of wearable devices 150A-150C may include one or more components for collecting gait information of a user, such as sole pressure sensors, accelerometers and gyroscopes. The wearable devices may also include notification means, such as an audio alarm, to warn a user of danger (e.g. unstable gait that could result in a proximate fall). In one example, each of the sets of wearable devices 150A-150C comprises a respective component for each foot of a user. However, in another example it may be sufficient to have a single wearable device for only one foot of a user. Notably, the users, and hence the sets of wearable devices 150A-150C, may move throughout the coverage area of local area network 140, thus benefiting from the ability of handing off between the ZigBee access points 141A-141E.

In one embodiment, the core network 110 may include an application server (AS) 114 and a database (DB) 116. Notably, AS 114 may perform some or all of the functions described herein in connection with determining a mode of motion. For example, AS 114 may collect and store in database 116 user gait information received from the one or more sets of wearable devices 150A-150C. Database 116 may also store user profiles including information on each user's age, weight, height, metabolic rate and so forth for the user. In addition, database 116 may also store test data, generic signatures for different modes of motion or types of activities, principal components (e.g., eigenfunctions comprising eigenvectors and/or eigenvalues) based upon the test data, disease/medical condition profiles, and so forth.

In one embodiment, gait information may be forwarded from local area network 140 via access network 120 and/or access network 130 to AS 114. At AS 114, the gait information may be collected, stored in database 116 and used for creating signatures/Hidden Markov Models (HMMs) for different modes of motion and/or for detecting a current mode of motion based upon one or more existing signatures, as described in connection with FIGS. 2-4. In one embodiment, the AS 114 may comprise a general purpose computer as illustrated in FIG. 5 and discussed below. Notably, AS 114 is suitable for performing some or all of the functions of the present disclosure for determining a mode of motion as described in greater detail below. In addition, although only a single AS 114 and a single DB 116 are illustrated in core network 110, it should be noted that any number of application servers 114 or databases 116 may be deployed.

In one embodiment, the gait information includes information which identifies a particular wearable device or set of wearable devices as a source of the gait information. The gait information may also include pressure information, acceleration information (including both linear and rotational accelerations), gyroscopic information, elevation information, time information and/or location information. In particular, raw gait information, such as pressure information, acceleration information, gyroscopic information, elevation information, temperature and fluid content (edema) may be collected from the various sensors of a wearable device. Other components may also contribute to the gait information prior to the gait information reaching AS 114. For example, each of the ZigBee access points 141A-141E may time stamp any gait information that is received from one of the sets of wearable devices 150A-150C. In addition, in one example the ZigBee access points 141A-141E may also append their location information to any gait information that is received. In another example, each ZigBee access point 141A-141E may simply append its own identity to any gait information that is received, where the identity information is sufficient to indicate the approximate location of the user relative to a corresponding ZigBee access point.

In one embodiment, AS 114 may also determine characteristics of motion information from the gait information. For example, AS 114 may gather gait information relating to a user over a period of time, e.g., over an hour, over a day, over a week, and so forth. From the gait information, AS 114 may then determine characteristics of motion such as a stride length, a speed, an acceleration, an elevation, and so forth, as well different modes of motion or different types of activities that a user is engaged in at various times within the time period. For example, accelerometers within one of the sets of wearable devices 150A-150C may indicate accelerations along different axes. Accordingly, the raw gait information may simply include an acceleration and an indication of which component recorded the acceleration. Different accelerations may then be vector summed by AS 114 to derive an overall acceleration magnitude and direction which may then be included as part of the characteristics of motion information.

Other characteristics of motion, such as speed and stride length, may also be determined from gait information in various ways. For instance, in one embodiment, global positioning system (GPS) location data is included in or appended to the gait information to allow a change in position over time to be determined. In this way, the average speed and speed at various times may be calculated. In addition, if the mode of motion is determined to be running or walking, the distance traveled in a particular time divided by a number of stances, e.g., steps, observed in the same time will indicate the average stride length. In another embodiment, one or more of the sets of wearable devices 150A-150C may include a pair of sensors, one for each foot, to determine a distance between the sensors. For example, the sensors can send and measure a round-trip time between the sensors, e.g., using infrared signals, radio frequency (RF) signals, acoustic signals, and the like to estimate a distance between the sensors.

In another embodiment, GPS location data may be unavailable. Accordingly, the gait information may include position information derived from one or more other sources. For instance, each of the ZigBee access points 141A-141E may append its identity and/or location information to any gait information that the ZigBee access point receives and forwards, thereby allowing AS 114 to determine the approximate location of a user at different times. For example, at a first time, gait information for the set of wearable devices 150A may be received and appended with the identity and/or location of ZigBee access point 141A. At a later time, gait information may be received for the same set of wearable devices 150A from ZigBee access point 141B. Thus, AS 114 can determine the approximate distance travelled, speed and so forth, based upon the difference in positions of the respective ZigBee access points.

The foregoing describes various functions of AS 114 (and database 116) in connection with embodiments of the present disclosure. However, it should be noted that in one example, local area network 140 may also include an application server (AS) 144 and a database 146 which may perform the same or similar functions to those of AS 114 in core network 110. In other words, AS 144 may also collect and store user gait information from the one or more sets of wearable devices 150A-150C via the ZigBee access points 141A-141E. Database 146 may also store user profiles, instructions relating to the tracking of different users, test data, generic signatures for different modes of motion or types of activities, principal components derived from the training data and so forth, to allow AS 144 to determine characteristics of motion information and/or to determine a mode of motion. In one embodiment local area network 140 also provides access for endpoint device 160, e.g., a personal computer, a laptop computer, tablet computer, smart phone, and the like to connect to AS 144 and/or AS 114. For example, a doctor, a nurse, a technician, a patient, and so forth may use endpoint device 160 to access AS 114 and/or AS 144. In one embodiment, endpoint device 160 is connected directly to local area network 140. However, in another embodiment, endpoint device may be a remote device that connects to network 140 and AS 144 via one or more of access network 120, access network 130 and or core network 110.

In one example, one or more of the set of wearable devices, e.g., set 150C, may also communicate with a cellular base station 121A and/or 121B of access network 120 to upload gait information to a server performing functions for determining a medical condition regression. For example, the set of wearable devices 150C may include a subscriber identity module (SIM) card, a cellular antenna and/or any other components that may be required to enable cellular communications via access network 120. Alternatively, or in addition, the set of wearable devices 150C may communicate with access network 120 via cellular device 151. For example, cellular device 151 may comprise an intermediary unit, such as a cell phone, a personal base station, a femtocell or the like, for providing a tethering function to the set of wearable devices 150C. In other words, the set of wearable device 150C and the cellular device 151 may communicate using various cellular communication standards or using near field communication techniques such as Wi-Fi/IEEE 802.11, Bluetooth, ZigBee and so forth. Regardless of the specific technology or communication techniques used, access network 120 may thus receive gait information from the set of wearable devices 150C and forward such information to a server performing functions for determining a medical condition regression of the present disclosure.

In one example, the gait information is uploaded to AS 114 in core network 110. However, in another example, the gait information may be passed to AS 144 in local area network 140. For example, one embodiment of the present disclosure may be managed via AS 144 in local area network 140 but still collects information from users who are not proximate to local area network 140 and/or are not within range to communicate directly with components of local area network 140.

In one embodiment, local area network 140 may comprise an indoor network, e.g., a combination of wired and wireless LANs within a user's home or of a medical facility such as a hospital, a rehabilitation center, an elder care facility, and the like. Thus, local area network 140 and access network 120 may be complimentary to one another, with local area network 140 providing the capability of uploading gait information while a user is indoors, and with the access network 120, e.g., a cellular network, providing coverage while the user is outdoors and/or while the user is outside of the communication range of the local area network 140.

In one embodiment, each of the sets of wearable devices 150A-150C may be configured to connect to local area network 140 and the ZigBee access points 141A-141E when available, and to connect to access network 120 only when local area network 140 is not available. In one example, when connecting to access network 120, the cellular device 151 may time stamp gait information as well as append to or include location information with the gait information that it receives and uploads to a network-based server, e.g., AS 114. For example, if the gait information is passed from the set of wearable devices 150C via a cellular phone to access network 120, the cellular phone may reveal the GPS location information of the phone. Thus, the GPS location information of the phone can be associated with the contemporaneous gait information of the set of wearable devices 150C. As an alternative, or in addition, each of the base stations 121A and 121B may calculate location information of the device from which it receives the gait information based upon cell tower triangulation, distance and direction estimation and so forth. Thus, when AS 114 and/or AS 114 receives gait information, regardless of whether it is received from local area network 140 or from access network 120, it may include location information and/or time information, in addition to the other parameters such as acceleration, pressure, and so forth obtained by the sensors of a set of wearable devices.

It should be noted that the network 100 has been simplified. For example, the network 100 may include other network elements (not shown) such as border elements, routers, switches, policy servers, security devices, gateways, administrator and user consoles, and so forth.

Figure 2:
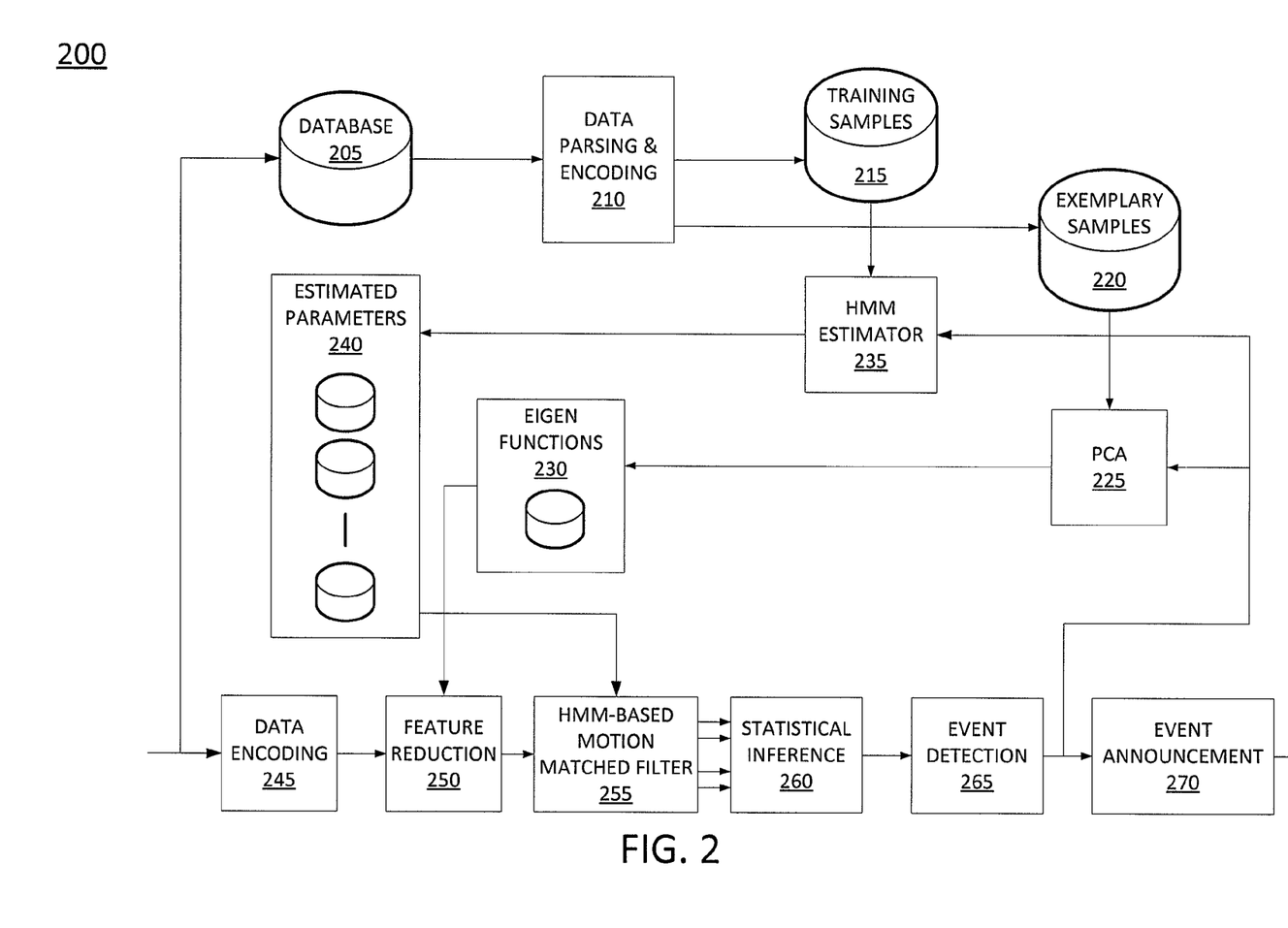
FIG. 2 illustrates an exemplary system for determining a mode of motion, according to the present disclosure.

FIG. 2 illustrates an exemplary system 200, referred to herein as a generalized analytic engine, in accordance with the present disclosure. In particular, the system 200 incorporates principal component analysis (PCA) with hybrid frequency-domain/time-domain based Markov models. In one embodiment, the system 200 may be implemented by any one or more of an application server, such as illustrated in FIG. 1, a computing device or system 500 and/or a processor 502 as described below in connection with FIG. 5.

The first component of system 200 is a database 205 which stores gait information from one or more users received from one or more wearable devices. In one embodiment, the gait information may be raw data from pressure sensors in the soles of a pair of shoes. In another embodiment, the gait information may include acceleration data, elevation data, gyroscopic data, and so forth. Notably, the system 200 may receive various types of data which can be used for training purposes. Thus, the gait information may include or be supplemented by further biometric information, such as electrocardiogram data, heart rate data, and so forth. In one embodiment, the database 205 receives and stores training data from one or more test subjects performing known modes of motion, which broadly encompass tasks, motions, stances and/or postures, e.g., running, jumping, standing, sitting, walking, falling, cycling, laying down, etc. For example, a test subject may walk for 60 seconds. The sensor data from the 60 second test phase may then comprise gait information/ test data that is stored in database 205. The test subject may then perform additional test runs for running, jogging, sitting, standing, cycling, lying down, etc. The same process may be repeated for various other test subjects such that all of the test data is eventually collected and stored in database 205.

Data parsing and encoding module 210 receives training data, i.e., gait information, from database 205 and performs one or more processing tasks on the training data. For example, data parsing and encoding module 210 may receive a stream of training data comprising a sequence of gait information for one of the test runs relating to a mode of motion. The module 210 may then break the gait information into defined segments of a particular duration and further define a frame of a selected number of segments to provide some coarseness to the data. In another example, data parsing and encoding module 210 may generate characteristics of motion information from the raw gait information and/or transform the gait information e.g., via Fourier transform, translation into polar coordinates, combining data from multiple linear orthogonal acceleration sensors into a single three-dimensional acceleration value, and so forth. Module 210 may repeat the process for a number of different sequences of gait information relating to each of a plurality of different modes of motion, e.g., from different test runs, from different test users and so forth.

Module 210 passes at least a portion of the processed training data to training samples module 215. Similarly, module 210 passes at least a portion of the processed training data to exemplary samples module 220. In one embodiment, each of the training samples module 215 and exemplary samples module 220 comprises a database. However, exemplary samples module 220 may receive selected training data that is of higher quality than the bulk of the training data processed by the data parsing and encoding module 210. For example, training data that is particularly pure, uniform, non-noisy, and so forth may be selected from a larger set of available training data and passed to the exemplary samples module 220. In addition, exemplary samples module 220 may receive samples relating to a number of different modes of motion such that Principal Component Analysis (PCA) module 225 may process a data set that spans a plurality of different modes of motion. On the other hand, training samples module 215 may receive a larger set of processed training data from data parsing and encoding module 210. In particular, the set of processed training data stored in training samples module 215 is for use by Hidden Markov Model (HMM) estimator module 235, which may work more accurately with increasing sizes of training data samples. In addition, HMM estimator module 235 processes training data relating to one mode of motion completely separate from training data relating to a second mode of motion. The purpose of the HMM estimator module 235 is to generate a separate HMM for each mode of motion. However, the purpose of the PCA module 225 is to determine principal components in a feature space that best captures variances in the entire gait information feature space.

PCA module 225 receives processed training data samples from exemplary samples module 220. Notably, one of the functions of PCA module 225 is to perform feature reduction of the training data. For example, the processed training data received from exemplary samples module 220 may be divided into time frames, and segments within each frame. Each segment may have a large number of samples, e.g., more than 100, from which a smaller number, such as less than 10, are selected based upon PCA. For example, the training data may be represented by a vector or matrix with each entry relating to a particular data point at a time within the segment. For example, training data may be generated by six pressure sensors in each shoe, a gyroscopic module for each foot and three accelerometers for each foot, generating 20 data points at any given time. If the frame is ten seconds, each segment is one second and the sampling is every 0.5 seconds, the total number of data points for a segment will be 40 data points, while the total number of data points for the frame will be 400 data points.

Note that data parsing and encoding module 210 may have already pre-processed the training data based upon design parameters such as described above. For example, if the incoming data comprises analog pressure information for one of several pressure sensors, data parsing and encoding module 210 may average the pressure information in any 0.5 second interval to provide one of the data points. In addition, as mentioned above, module 210 may have combined certain data, e.g., into "characteristics of motion information", such as combining three sources of linear acceleration data for one foot into a single three-dimensional acceleration. Thus, data parsing and encoding module 210 may reduce the total number of data points in the processed training data fed to the PCA module 225. However, this still leaves a large number of data points for a segment. Accordingly, PCA reduces the number of data points to a defined number of "most relevant" features of the training data in any segment.

In particular, PCA module 225 uses covariance matrix analysis to identify the eigenfunctions, which are the principal components. Notably, PCA involves feature reduction, reducing the number of variables or data points, by transforming the data points to uncorrelated variables. PCA preserves as much variance in the data as possible, but reduces noise through the assignment of noise components to smaller eigenvalues. Mathematically, for a zero-expectation p-dimensional random vector y, its principal component transform is an orthogonal transformation to a lower d-dimensional subspace that un-correlates components of y, maximizes variance in the projected space and minimizes the mean-square error of the representation. The principal component transform is generated as the projection onto the subspace spanned by the d-largest eigenvectors of the covariance matrix of y. PCA can be considered as the discrete-time equivalent of the Kahrunen-Loeve expansion (Fourier transform) of a continuous time random process on a bounded time interval.

If y is a vector representing a number of data points, p, from the training data for a given segment, then the covariance matrix for y is a symmetric p-by-p matrix where each row and column corresponds to one of the data points. The diagonal represents the variance for a particular data point, and each of the non-diagonal values represent the covariance between the two data points represented by the respective row and column for the entry. To create the covariance matrix in the first instance, the training data for any segment within the frame is represented as a vector of data points, y. The length, or size of the vector is p, the number of data points. A p-by-n matrix, M, is then constructed, where n is the number of sample sets from the training data (e.g., each column is a length p vector corresponding to the data points observed during the respective time segment, n is also the number of vectors corresponding to the number of samples and/or frame length). The covariance matrix is then given as $C_M=(1/(n-1))MM^T$, where $C_M$ is the covariance matrix of size p-by-p and $M^T$ is the transpose of matrix M.

PCA module 225 then finds the eigenvalues and eigenvectors of the covariance matrix $C_M$. In other words, PCA involves linear reduction of the features space into a defined number of orthogonal dimensions that best captures the variance of the data, where an eigenvector is a linear combination of two of the original "dimensions". PCA module 225 may further arrange the eigenvectors into a principal component transform matrix, where the eigenvectors are ordered from largest eigenvalue to smallest eigenvalue. The eigenvalue is a scalar which represents the relative importance or impact of each eigenvector. Thus, the eigenvector with the largest eigenvalue is a vector pointing in a direction within the p-dimensional space where the original data shows the greatest variance. This is deemed to be the most important dimension and is thus referred to as the first principal component, or principal component 1. The eigenvector with the second largest eigenvalue is a vector that is perpendicular, or orthogonal, to the first eigenvector, and points in a direction in the p-dimensional space that captures a second greatest variance of the data.

Thus, the first eigenvector, second eigenvector and so forth, are used to form the principal component transform matrix. PCA module 225 may further select a number of principal components, d, that is less than the number of dimensions in the original feature space, p, for inclusion in the principal component transform matrix. In particular, d is the number of columns of the principal component transform matrix, where d is selected based upon the number desired components (dimensions) in a reduced data set. Thus, PCA is used to reducing a large quantity of the raw gait information to a smaller set of data that can be processed more quickly and with less resources. When the principal component transform matrix is applied to the matrix M, representing the original data set, a reduced data set is created, where the original matrix M is projected into a d-dimensional space and where the axes correspond to the principal component/eigenvector directions. The principal component transform matrix is passed from PCA module 225 to the eigenfunction storage module 230 where is it stored for use in testing phase processing (described in greater detail below in connection with feature reduction module 250).

As mentioned above, HMM estimator module 235 receives training data samples from training samples module 215. The purpose of the HMM module 235 is to generate a Hidden Markov Model (HMM) for each particular mode of motion/type of activity based upon the training data. The HMM for each mode of motion thus comprises a unique signature for the mode of motion. In particular, embodiments of the present disclosure consider that gait information for a particular mode of motion can be represented as a Markov process with unobserved (hidden) states corresponding to different phases within a gait cycle. A Markov system can be modeled as series of states and a probability of transitions between the states. However, in a hidden Markov system, the states are not directly observed. Rather, the hidden states may be revealed by a series or sequence of outputs. Thus, a HMM includes a set of hidden states, a probability of transition between states (transition probability) and a probability of output of a given state (emission probability), as well as other parameters described below.

Figure 3:
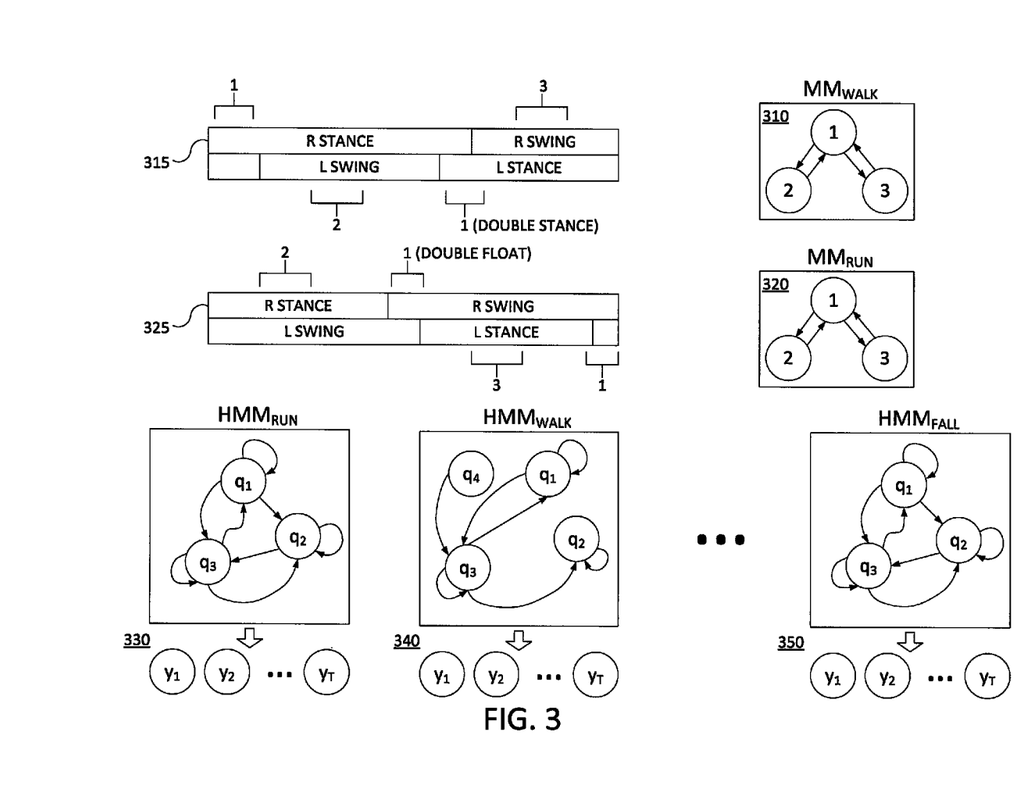
FIG. 3 illustrates representations of exemplary Markov systems and related gait cycles, according to the present disclosure.

To further aid in understanding the present disclosure, FIG. 3 illustrates exemplary Markov systems for walking mode 310, and for running mode 320. The timing sequence 315 shows the assumed actual phases for the gait cycle of walking. It includes three phases: (1) double stance, where both feet are standing on the ground; (2) left swing, where the left foot swings forward and the right foot remains planted on the ground; and (3) right swing, where the right foot swings forward and the left foot remains planted on the ground. The Markov system for walking mode 310 thus includes the three states corresponding to the phases of the gait cycle shown in sequence 315, along with the transitions between the states. Similarly, the timing sequence 325 illustrates phases of a running gait cycle: (1) a double float, with both feet off the ground; (2) left swing, with the left foot swinging forward and the right foot on the ground; and (3) right swing, with the right foot swinging forward and the left foot planted on the ground. The Markov system for running mode 320 thus includes these three hidden states, along with the transitions between the states.

In practice, the phases of the gait cycle are not directly provided by the sensor data/gait information. For example, the sensor data may comprise multiple pressure sensors and accelerometers attached to two shoes. Thus, the system 200 may simply receive raw pressure and acceleration data. To account for this circumstance, Hidden Markov Models (HMMs) are Markov systems with a number of states (hidden states), transition probabilities between states, and emission probabilities for observing certain outputs in connection with each of the hidden states. For example, HMMs 330, 340 and 350 on the bottom of FIG. 3 each shows a number of hidden states $q_1, q_2, q_3 \ldots$, the possible transitions between the hidden states and the corresponding observations which may correspond to each hidden state, $y_1, y_2 \ldots y_t$.

More specifically, HMMs are generally characterized by five parameters:

N—the number of states (in the present example, N is the number of states in a gait cycle).

M—the number of observation symbols per state.

A—a state transition probability distribution or matrix; $A=\{a_{ij}\}$ where $a_{ij}$ is the probability of transitioning from any state i to any state j. In some HMM systems, there may be no transitions from a particular one of the states to another particular one of the states. Thus, there may be some elements in A with a value of zero (i.e., zero probability of transition from state i to state j).

B—a observation symbol probability distribution; for each state j, the probability of observing one of the possible observation symbols.

π—initial state probability distribution; the likelihood of starting in any particular state.

Collectively, the HMM is characterized by the parameter set $\lambda=(N, M, A, B$ and $\pi)$. N and M may be considered design parameters, e.g., selected by a system operator. Thus, a HMM may also be characterized by a shorthand notation $\lambda=(A, B$ and $\pi)$, where A, B and π may be experimentally determined from a set of training data. For example, to place limits on parameter M, a system designer will know the range of pressures that may be registered by each pressure sensor. Thus, there may be limits placed on the range of values that this particular observation symbol may take. Similarly, the designer may choose to allow only discrete values for particular observation symbols. For instance, the designer may pre-process acceleration data such that is rounded or truncated to one decimal point accuracy. In addition, parameter N, the number of states may be provided as input to the system 200 by a designer. For example, a designer may have prior knowledge of, and/or the ability to estimate the number of phases in the gait cycle of a particular mode of motion.

In any case, using the parameter set $\lambda=(N, M, A, B$ and $\pi)$, the HMM can be applied to determine the probability of a given observation sequence. Essentially, the probability of a certain sequence of observations may be predicted by the HMM based upon the collective probabilities of the individual transitions from each state to the next state in the sequence. In this case, the training data provides an observation sequence. Initial values for A, B and π are selected, e.g., based upon educated guesses/estimates. Then the probability of the observation sequence from the HMM using the initial values for A, B and π (as well as N and M) is calculated.

In general, A, B and π may be iteratively adjusted to compare a current HMM parameter set to a possible updated HMM parameter set. If a new set of A, B and TT provides a better fit to the observed data, then the new set of A, B and π is saved as the HMM parameters. In other words, A, B and π are adjusted to maximize the probability of the sequence of observations being generated by the HMM. Various algorithms may be employed to execute this general but complex process. For example, an expectation maximization (EM) algorithm, a Baum-Welch algorithm, a forward-backward algorithm and so forth, may be employed. In one embodiment, a Baum-Welch algorithm is implemented using a Gaussian Mixture Model (GMM) with spherical covariance. Following this iterative process, a finalized parameter set A=(N, M, A, B and π) is passed to the estimated parameters storage module 240 where the HMM for the particular mode of motion is stored for use in testing phase processing (e.g., as described in greater detail below in connection with HMM motion matched filter 255).

The above has described the processing path from database 205 to the estimated parameters storage module 240 with respect to training data for a single mode of motion. Thus, it should be noted that the same process may be followed with respect to each of a plurality of different modes of motion, e.g., to estimate parameters and to generate a separate and unique HMM for each mode of motion.

Modules 245 to 270 represent the testing phase components of system 200. In one embodiment, once eigenfunctions/principal components and the estimated parameters/HMMs for each of number of different modes of motion are generated, these parameters may then be used to classify newly observed unstructured data. In particular, to some extent it is necessary for the training data to be labeled or assigned to different modes of motion in advance of the training phase processing. However, the testing data may be categorized without any supervision and without any external guidance as to the particular mode of motion underlying the incoming testing data.

First, data encoding module 245 processes the incoming testing data, e.g., gait information from sensors of a wearable device. For example, the gait information may be segmented into equal time intervals/segments within a time frame in the same manner as performed by data parsing encoding module 210, described above. The gait information may be preprocessed in various other ways as well, e.g., rounding or truncating to discrete values, removing outliers to smooth the data, performing non-linear transforms of the data, e.g., Fourier transform to provide frequency domain data, and so forth. In general, the preprocessing by module 245 follows the same scheme implemented by module 210. For each time segment within a frame, data encoding module 245 may vectorize the gait information data points. Data encoding module 245 may further generate a test data matrix with each column comprising a vector for a respective segment within the frame. The number of columns of the test data matrix is thus the number of time segments within the frame.

Feature reduction module 250 takes the test data matrix created by data encoding module 245 and applies the principal component transform matrix (with eigenvectors), to the test data matrix, resulting in a vector transformation or "change of basis" of the test data matrix. For example, the principal component transform matrix may be received from eigenfunction storage module 230. The change of basis transforms the data points to a set of axes that correspond to the principal components/eigenvectors of the principal component transform matrix. The number of data points in each column of the transformed test data matrix is reduced to the number d, the number of principal components selected for the reduced feature set and the number of dimensions in the transformed feature space.

The transformed test data matrix is then passed to the HMM-based motion matched filter 255. HMM-based motion matched filter 255 takes frames of x segments (e.g., 10 segments) and calculates the probability that the sequence would be output if the mode of motion is running, if the mode of motion is walking, and so forth. The x segments may include data relating to different phases in the gait cycle, and thus, different states in the HMM for the correct mode of motion. Each HMM is applied to the observed data sequence and a probability of the sequence being observed, given the HMM, is generated. In one embodiment, HMM-based motion matched filter 255 applies a sliding window, e.g., frames of x segments, to a sequence of the test data, and iteratively re-applies the HMM to the sequence within the sliding window. For example, the sliding window may look at a sequence of x segments to calculate a first probability/likelihood. The sliding window may then be advanced one segment, two segments, etc., and a second probability/likelihood calculated, and so forth, up to a desired number of window advances. The HMM-based motion matched filter 255 may then average or otherwise combine the probabilities for each of a plurality of different probability/likelihood calculations for each of the different windows to give a composite score.

Statistical inference module 260 receives the calculations from HMM-based motion matched filter 255 and determines the HMM that provided the highest probability of the given sequence from the selected x segments and/or from the sliding window. In one embodiment, statistical inference module 260 implements a Bayesian inference of the HMM that best predicts the observed data.

Event detection module 265 determines the mode of motion that matches the testing data based upon the result of the Bayesian inference from the statistical inference module. In one embodiment, event detection module 265 only selects a particular mode of motion to output when the confidence of the statistical inference is greater than a particular threshold. In addition, in one embodiment, event detection module 265 may apply a Viterbi algorithm to the observed sequence of test data to determine the most likely state path through the best match HMM. In one embodiment, the plausibility of the selected HMM is checked against the most likely path selected by the Viterbi algorithm. For example, if a HMM is selected as a best match for predicting the received test data, but the most likely path follows a series of disfavored/unlikely transitions, then there may be a problem with the test data or a problem somewhere in system 200 that is affecting the categorization. In any case, if event detection module 265 deems the result of the statistical inference to be satisfactory, the resulting mode of motion corresponding to the best match HMM is passed to event announcement module 270, which may output the result to a database, transmit a notification to a monitoring computer or other device, and so forth.

It should also be noted that the system 200 may continue to update the principal components and/or the HMMs for each mode of motion as it continues to process new data. In other words, "testing" data may also comprise additional training data that is used to further refine the principal components and HMMs. For example, high quality results from the event detection module 265 may be fed to database 205 for use in updating the HMMs and/or eigenfunctions that are in use in system 200. For instance, classification results with a sufficiently high confidence level based upon the Bayesian inference may be fed back to provide further training to system 200.

Figure 4:
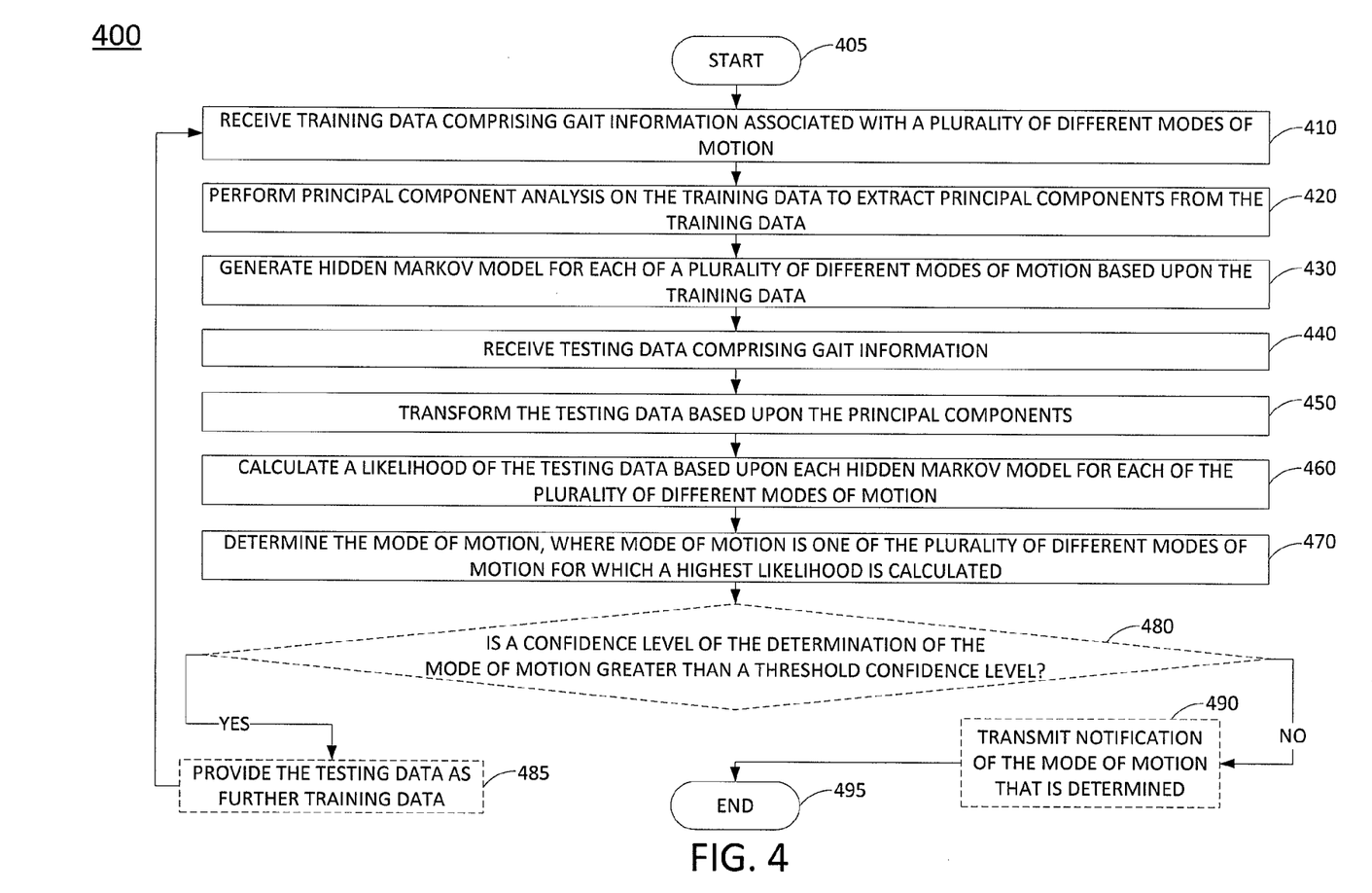
FIG. 4 illustrates an example flowchart of a method for determining a mode of motion, according to the present disclosure.
Figure 5:
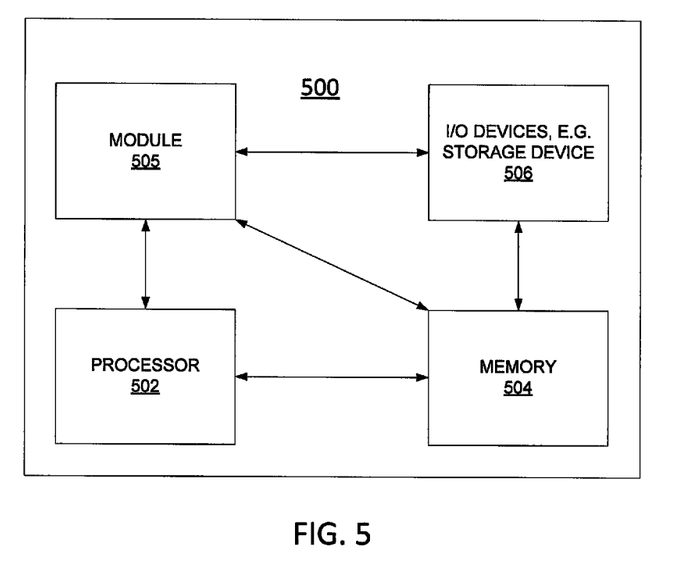
FIG. 5 illustrates a high-level block diagram of a general-purpose computer suitable for use in performing the functions described herein.

FIG. 4 illustrates an example flowchart of one embodiment of a method 400 for determining a mode of motion, according to the present disclosure. In one embodiment, the method 400 may be performed by an application server such as AS 114 or AS 144 illustrated in FIG. 1. In one embodiment, the steps, functions, or operations of method 400 may be performed by a computing device or system 500, and/or processor 502 as described in connection with FIG. 5 below. For illustrative purpose, the method 400 is described in greater detail below in connection with an embodiment performed by a processor, such as processor 502.

The method 400 begins at step 405 and proceeds to step 410. At step 410, the method receives training data comprising gait information associated with a plurality of different modes of motion. For example, a set of wearable devices may collect gait information from a number of sensors such as linear accelerometers, gyroscopes, pressure sensors and the like. The processor may receive the gait information from the set of wearable devices via one or more intermediary network such as a local network, e.g., a local area network (LAN) that may comprise a ZigBee mesh network, a wired and/or a wireless/cellular access network, and so forth. In one example, the training data is collected from sensors worn by a plurality of users/test subjects performing known modes of motion. For example, each user may be asked to walk for 60 second, run for 60 seconds, stand for 60 seconds, sit for 60 seconds, cycle for 60 seconds, etc.

At step 420, the method performs Principal Component Analysis (PCA) on the training data to extract principal components from the training data. For example, as described above, PCA may involve processing training data that spans a plurality of different modes of motion. In one embodiment, the gait information may be divided into time frames and time segments, where the gait information is vectorized into a plurality of "feature vectors" representing the data for each segment. In turn, the feature vectors may be used to generate a matrix with a number of columns corresponding to the frame length. A covariance matrix may be generated from this matrix of feature vectors and a plurality of principal components (eigenfunctions) calculated from the covariance matrix.

At step 420, the method may further generate a principal component transform matrix comprising a selected number of eigenvectors. For example, if ten eigenfunctions are generated, the principal component transform matrix may be selected to include only a subset, such as the top five eigenvectors (based upon the magnitudes of the respective eigenvalues), the top three eigenvectors, and so forth. Thus, step 420 may involve reducing the number of data points to a defined number of "most relevant" features of the training data in any segment.

At step 430, the method generates a Hidden Markov Model (HMM) for each of a plurality of different modes of motion based upon the training data. For example, embodiments of the present disclosure consider that gait information for a particular mode of motion can be represented as a Markov process with unobserved (hidden) states corresponding to different phases within a gait cycle. For example, a HMM may be characterized by the parameter set $\lambda=(N, M, A, B$ and $\pi)$ where N is the number of states (in this case, phases in a gait cycle), M is the number of observation symbols per state, A is a state transition probability distribution matrix, B is an observation symbol probability distribution, and $\pi$ is an initial state probability distribution. The parameters N and M may be set in advance by a system operator or designer. Thus, in one example, the processor may receive N and M as inputs at step 430. However, parameters A, B and $\pi$ may be determined by the processor at step 430 using the training data received at step 410. In particular, the processor may use a portion of the training data received at step 410 that corresponds to one particular mode of motion. For instance, since the training data may be generated by test subjects performing known modes of motion, the training data may be pre-labeled as being associated with a particular mode of motion.

In one example, at step 430 the method may start with an initial estimate of the HMM using the parameters A, B and $\pi$, and calculate a likelihood of observing a sequence of the training data. For example, A, B and 7 may be estimates that comprise further inputs that are received at step 430. The processor may then iteratively adjust one or more of A, B and $\pi$ to compare a current HMM parameter set to a possible updated HMM parameter set. If a new set of A, B and $\pi$ provides a better fit to the observed data (e.g., the training data), then the new set of A, B and $\pi$ is saved as the HMM parameters and replaces the previous estimate. In other words, A, B and $\pi$ are adjusted to maximize the probability of the sequence of observations being generated by the HMM. Various algorithms may be employed to implement this process, including: an expectation maximization (EM) algorithm, a Baum-Welch algorithm, a Baum-Welch algorithm using a Gaussian Mixture Model (GMM) with spherical covariance, a forward-backward algorithm, and so forth. It should be noted that this process is repeated for training data associated with each of a plurality of different modes of motion to generate separate and unique HMMs for each mode of motion, e.g., running, jumping, standing, sitting, falling, cycling, lying down, and so on.

At step 440, the method receives testing data comprising gait information. For example, the testing data may comprise the same general type of gait information that comprises the training data received at step 410. However, the testing data may be unstructured, e.g., without any prior knowledge of the mode of motion which generated the training data.

At step 450, the method transforms the testing data based upon the principal components. For example, the principal components extracted at step 420 may comprise a principal component transform matrix. Thus, in one example, the processor generates a test data matrix from the test data in a given time frame and applies principal component transform matrix (with eigenvectors), to the test data matrix, resulting in a vector transformation or "change of basis" of the test data matrix. In one embodiment, the number of dimensions in the test data is reduced depending upon the number of eigenvectors that are included in the principal component transform matrix. Advantageously, this allows the method to balance implement fast operation on a reduced feature set while maintaining most of the accuracy of the full data set. In fact, the reduced feature set may in some cases enhance the accuracy of the method insofar as noise components relegated to smaller eigenvalues and may be removed from the data.

At step 460, the method calculates a likelihood of the testing data based upon each HMM for each of the plurality of different modes of motion. For example, the processor may take a frame of x segments (e.g., 10 segments) and calculate the probability that the sequence would be output if the mode of motion is running, if the mode of motion is walking, and so forth. The x segments may include data relating to different phases in the gait cycle, and thus, different states in the HMM for the correct mode of motion. Each HMM is applied to the observed data sequence and a probability of the sequence being observed, given the HMM, is generated. It should be noted that in one embodiment, the frames of x segments relate to transformed testing data comprising a reduced feature set (e.g., as generated at step 460). Thus, in one example the likelihood/probability calculations at step 460 are made for each HMM with respect to the transformed testing data.

At step 470, the method determines the mode of motion that is associated with the testing data. For example, the HMM/mode of motion for which a highest likelihood score is generated may be declared to be the mode of motion associated with the testing data.

At optional step 480, the method determines whether a confidence level of the determination of the mode of motion is greater than a threshold confidence level. For example, the mode of motion that is determined at step 470 may have a likelihood/probability calculation that is only slightly greater than the calculations from the HMMs for one or more of the other candidate modes of motion. As such, the mode of motion/HMM generating the highest likelihood score may have only just narrowly prevailed over the other choices. As such, the method may account for the relative magnitude of the likelihood score for the mode of motion that is selected versus one or more of the other modes of motion. In one embodiment, the threshold may be selected by a system operator or designer. If the confidence level is less than the threshold, the method 400 may proceed to step 490 and/or step 495. However, if the confidence level is greater than the threshold, then the method may proceed to optional step 485.

At optional step 485, the method provides the testing data as further training data. For example, if there is a high confidence that the testing data is correctly classified as a specific mode of motion, then this gait information can be used to update the HMMs and/or the principal components that are calculated and implemented in the preceding steps. On the other hand, if the processor is not confident in the determination of the mode of motion, then there may be a greater risk in training the HMM and principal component parameters upon potentially erroneously classified gait information.

At optional step 490, the method may transmit a notification of the mode of motion that is determined at the prior step 470. In other words, depending upon the determination at step 470, the processor may notify the user, a medical provider, a caregiver, a physical therapist, etc.

Following any one of steps 470, 480 or 490, the method 400 may proceed to step 495 where the method ends.

It should be noted that although not explicitly specified, one or more steps, operations or blocks of the method 400 described above may include a storing, displaying and/or outputting step as required for a particular application. In other words, any data, records, fields, and/or intermediate results discussed in the methods can be stored, displayed, and/or outputted to another device as required for a particular application. Furthermore, steps, operations or blocks in FIG. 4 that recite a determining operation, or involve a decision, do not necessarily require that both branches of the determining operation be practiced. In other words, one of the branches of the determining operation can be deemed as an optional step. Furthermore, operations, steps or blocks of the above described methods can be combined, separated, and/or performed in a different order from that described above, without departing from the example embodiments of the present disclosure.

FIG. 5 depicts a high-level block diagram of a general-purpose computer suitable for use in performing the functions described herein. As depicted in FIG. 5, the system 500 comprises a hardware processor element 502 (e.g., a central processing unit (CPU), a microprocessor, or a multi-core processor), a memory 504, e.g., random access memory (RAM) and/or read only memory (ROM), a module 505 for determining a mode of motion, and various input/output devices 506 (e.g., storage devices, including but not limited to, a tape drive, a floppy drive, a hard disk drive or a compact disk drive, a receiver, a transmitter, a speaker, a display, a speech synthesizer, an output port, an input port and a user input device (such as a keyboard, a keypad, a mouse, a microphone and the like)). Although only one processor element is shown, it should be noted that the general-purpose computer may employ a plurality of processor elements. Furthermore, although only one general-purpose computer is shown in the figure, if the method(s) as discussed above is implemented in a distributed manner for a particular illustrative example, i.e., the steps of the above method(s) or the entire method(s) are implemented across multiple general-purpose computers, then the general-purpose computer of this figure is intended to represent each of those multiple general-purpose computers.

It should be noted that the present disclosure can be implemented in software and/or in a combination of software and hardware, e.g., using application specific integrated circuits (ASIC), a general purpose computer or any other hardware equivalents, e.g., computer readable instructions pertaining to the method(s) discussed above can be used to configure a hardware processor to perform the steps, functions and/or operations of the above disclosed methods. In one embodiment, instructions and data for the present module or process 05 for determining a mode of motion (e.g., a software program comprising computer-executable instructions) can be loaded into memory 04 and executed by hardware processor element 502 to implement the steps, functions or operations as discussed above in connection with the exemplary system 200 and/or method 400. The processor executing the computer readable or software instructions relating to the above described method(s) can be perceived as a programmed processor or a specialized processor. As such, the present module 505 for determining a mode of motion (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. More specifically, the computer-readable storage device may comprise any physical devices that provide the ability to store information such as data and/or instructions to be accessed by a processor or a computing device such as a computer or an application server. In addition, it should be noted that the hardware processor can be configured or programmed to cause other devices to perform one or more operations as discussed above. In other words, the hardware processor may serve the function of a central controller directing other devices to perform the one or more operations as discussed above.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:
1. A method for determining a mode of motion, the method comprising:
   receiving, by a processor, training data, wherein the training data comprises gait information associated with a plurality of different modes of motion;

performing, by the processor, principal component analysis on the training data to extract principal components from the training data;

generating, by the processor, a hidden markov model for each of a plurality of different modes of motion based upon the training data;

receiving, by the processor, testing data comprising gait information;

transforming, by the processor, the testing data based upon the principal components;

calculating, by the processor, a likelihood of the testing data based upon each hidden markov model for each of the plurality of different modes of motion;

determining, by the processor, the mode of motion of the testing data, wherein the mode of motion is one of the plurality of different modes of motion for which a highest likelihood is calculated;

determining, by the processor, a most likely state path for the testing data through the hidden markov model for the mode of motion; and outputting, by the processor, the mode of motion that is determined when the most likely state path does not follow a disfavored state transition of the hidden markov model for the mode of motion.

2. The method of claim 1, wherein the performing principal component analysis comprises:
generating a matrix comprising a plurality of feature vectors from the training data;
generating a covariance matrix from the matrix comprising the plurality of features vectors; and
calculating eigenvectors for the covariance matrix.

3. The method of claim 2, wherein the performing principal component analysis further comprises:
generating a principal component transform matrix from the eigenvectors for the covariance matrix.

4. The method of claim 3, wherein the principal component transform matrix includes a subset of the eigenvectors for the covariance matrix that is less than a total number of the eigenvectors for the covariance matrix.

5. The method of claim 4, wherein the transforming the testing data based upon the principal components comprises:
generating a feature vector from the testing data; and
applying the principal component transform matrix to the feature vector that is generated from the testing data.

6. The method of claim 1, wherein the generating the hidden markov model for each of a plurality of different modes of motion based upon the training data comprises:
generating the hidden markov model for one of the plurality of different modes of motion based upon a portion of the training data associated with the one of the plurality of different modes of motion.

7. The method of claim 6, wherein the generating the hidden markov model for the one of the plurality of different modes of motion comprises:
generating an initial estimate of the hidden markov model for the one of the plurality of different modes of motion based upon a plurality of inputs.

8. The method of claim 7, wherein the plurality of inputs comprises:
a number of states of the hidden markov model;
a number of observation symbols per state;
an initial state transition probability distribution;
an initial observation probability distribution; and
an initial state probability distribution.

9. The method of claim 7, wherein the generating the hidden markov model for the one of the plurality of different modes of motion further comprises:

calculating a likelihood of a sequence of the training data based upon the initial estimate of the hidden markov model for the one of the plurality of different modes of motion;

modifying one of the inputs to generate an updated estimate of the hidden markov model for the one of the plurality of different modes of motion;

calculating a likelihood of the sequence of the training data based upon the updated estimate of the hidden markov model for the one of the plurality of different modes of motion; and replacing the initial estimate with the updated estimate when the likelihood of the sequence of the training data based upon the updated estimate is greater than the likelihood of the sequence of the training data based upon the initial estimate.

10. The method of claim 7, wherein the generating the hidden markov model for the one of the plurality of different modes of motion further comprises:
updating the initial estimate of the hidden markov model for the one of the plurality of different modes of motion using an expectation maximization algorithm.

11. The method of claim 10, wherein the expectation maximization algorithm comprises a Baum-Welch algorithm.

12. The method of claim 10, wherein the expectation maximization algorithm comprises a forward-backward algorithm.

13. The method of claim 1, further comprising:
providing the testing data as further training data when a confidence level of the determining of the mode of motion is greater than a threshold confidence level.

14. The method of claim 1, wherein the gait information comprises:
pressure information.

15. The method of claim 14, wherein the gait information further comprises at least one of:
acceleration information; and
gyroscopic information.

16. The method of claim 1, wherein the gait information is generated by a pair of foot-mounted sensors.

17. The method of claim 1, wherein the gait information of the training data and the gait information of the test data is time stamped prior to the gait information being received by the processor.

18. The method of claim 1, further comprising:
transmitting a notification of the mode of motion that is determined.

19. A computer-readable storage device storing instructions which, when executed by a processor, cause the processor to perform operations for determining a mode of motion, the operations comprising:
receiving training data, wherein the training data comprises gait information associated with a plurality of different modes of motion;
performing principal component analysis on the training data to extract principal components from the training data;
generating a hidden markov model for each of a plurality of different modes of motion based upon the training data;
receiving testing data comprising gait information;
transforming the testing data based upon the principal components;
calculating a likelihood of the testing data based upon each hidden markov model for each of the plurality of different modes of motion;

determining the mode of motion of the testing data, wherein the mode of motion is one of the plurality of different modes of motion for which a highest likelihood is calculated;

determining a most likely state path for the testing data through the hidden markov model for the mode of motion; and outputting the mode of motion that is determined when the most likely state path does not follow a disfavored state transition of the hidden markov model for the mode of motion.

20. An apparatus for determining a mode of motion, the apparatus comprising:

a processor; and a computer-readable medium storing instructions which, when executed by the processor, cause the processor to perform operations, the operations, comprising:

receiving training data, wherein the training data comprises gait information associated with a plurality of different modes of motion;

performing principal component analysis on the training data to extract principal components from the training data;

generating a hidden markov model for each of a plurality of different modes of motion based upon the training data;

receiving testing data comprising gait information;

transforming the testing data based upon the principal components;

calculating a likelihood of the testing data based upon each hidden markov model for each of the plurality of different modes of motion;

determining the mode of motion of the testing data, wherein the mode of motion is one of the plurality of different modes of motion for which a highest likelihood is calculated;

determining a most likely state path for the testing data through the hidden markov model for the mode of motion; and outputting the mode of motion that is determined when the most likely state path does not follow a disfavored state transition of the hidden markov model for the mode of motion.

* * * * *